United States Patent [19]

Joustra et al.

[11] 4,118,428

[45] Oct. 3, 1978

[54] PREPARATION OF ALKYL CHLORIDES

[75] Inventors: Annie H. Joustra; Teunis P. La Haye; Fernand H. Kesselaar, all of Amsterdam, Netherlands

[73] Assignee: Shell Oil Company, Houston, Tex.

[21] Appl. No.: 764,835

[22] Filed: Feb. 2, 1977

[30] Foreign Application Priority Data

Feb. 19, 1976 [GB] United Kingdom ............... 6604/76

[51] Int. Cl.$^2$ .......................................... C07C 17/08
[52] U.S. Cl. ................................ 260/663; 260/671 B
[58] Field of Search ........................... 260/663, 671 B

[56] References Cited

U.S. PATENT DOCUMENTS

| | | | |
|---|---|---|---|
| 2,328,275 | 8/1943 | Heard | 260/663 |
| 2,434,094 | 1/1948 | Axe | 260/663 |
| 3,395,188 | 7/1968 | Shook | 260/663 |
| 3,412,161 | 11/1968 | Bakker et al. | 260/663 |

*Primary Examiner*—C. Davis

[57] ABSTRACT

2-chloroalkanes are selectively prepared from detergent range alpha olefins i.e., olefins in the $C_7$ to $C_{30}$ range, by reacting the alpha olefin with hydrogen chloride in the presence of a metal chloride catalyst supported on a carrier having an average pore diameter of at least 30 millimicrons (m$\mu$).

9 Claims, No Drawings

PREPARATION OF ALKYL CHLORIDES

BACKGROUND OF THE INVENTION

This invention relates to a process for the preparation of secondary alkyl chlorides from alpha olefins. More particularly, this invention is directed to a method for the selective conversion of alpha olefins in the detergent range into 2-chloroalkanes by reaction with hydrogen chloride in the presence of a metal chloride catalyst supported on a porous carrier having a critically high average pore diameter.

Secondary alkyl chlorides are a well known class of organic compounds having a variety of utilities in commerce e.g. solvents, reaction intermediates, etc. It has long been known that secondary alkyl chlorides can be prepared from mono-olefins and hydrogen chloride by reacting the same in the presence of a metal chloride catalyst. For example, U.S. Pat. No. 2,103,692 discloses the hydrochlorination of the more reactive $C_2$ to $C_6$ olefins by vapor phase reaction with hydrogen chloride in the presence of certain di-and polyvalent metal chlorides e.g. $ZnCl_2$ supported on carriers such as silica gel or activated silica acid. U.S. Pat. No. 2,705,734 extends this hydrochlorination reaction to the liquid phase through the employment of zinc chloride catalyst in the form of zinc chloride-hydrocarbon addition compounds or aqueous zinc chloride solutions.

A particularly useful class of secondary alkyl chlorides are the chloroalkanes derived from detergent range olefins i.e. monoolefins in the $C_7$ to $C_{30}$ range. Specifically, the 2-chloroalkanes derived from alpha olefins in this range may be used to prepare tertiary amines from which amine oxides, quanternary ammonium salts and zwitterionic detergents e.g. betaines and sulfobetaines may be prepared. In this regard, it would be desirable if this class of 2-chloroalkanes could be prepared by direct hydrochlorination of the detergent range alpha olefins in the presence of a supported metal halide catalyst because of the obvious advantages of the use of heterogeneous solid catalysts in large scale processes. However, one difficulty which is encountered in the hydrochlorination of detergent range alpha olefins using metal halide catalysts, e.g. $ZnCl_2$ or $ZnCl_2$, supported on ordinary carriers (e.g. ordinary silica which has an average pore diameter of usually below 20 m$\mu$) is that isomerization of the olefins may take place resulting in the formation of an undesirable variety of secondary chlorides. For example, the hydrochlorination of alpha-olefins not only results in 2-chloroalkanes but also significant amounts of 3-and other internal chloroalkanes.

The present invention substantially overcomes the aforementioned deficiency in the catalytic hydrochlorination process of the prior art and, as a result, the invention provides an excellent means of obtaining 2-chloroalkanes in high selectivity from detergent range alpha olefins.

SUMMARY OF THE INVENTION

It has now been found that 2-chloroalkanes can be synthesized in greater selectivity from detergent range alpha olefins by hodrochlorination in the presence of a supported metal chloride catalyst if the metal chloride is supported on a carrier having an average pore diameter of at least 30 millimicrons (m$\mu$).

Accordingly, the present invention provides a process for the preparation of 2-chloroalkanes in high selectivity from detergent range alpha olefins which comprises reacting an alpha in the $C_7$ to $C_{30}$ range, or mixture of such olefins, with hydrogen chloride in the presence of a metal chloride supported on a carrier having an average pore diameter of at least 30 m$\mu$.

DESCRIPTION OF THE PREFERRED EMBODIMENTS

The olefin reactant employed in the process of the invention is suitably an alpha olefin or mixture of alpha olefins in the $C_7$ to $C_{30}$ carbon number range. Preferably, the olefin reactant is an alpha olefin containing 8 to 18 carbon atoms or a mixture of such olefins. It is also preferred that the alpha olefin be a linear alpha olefin or mixture of linear alpha olefins in the above defined carbon number range. Such olefin reactants can be obtained from a variety of conventional sources including ethylene oligomerization according to the processes described in U.S. Pat. Nos. 3,825,615, 3,737,475 and 3,686,351.

Suitable metal chloride catalysts for the process of the invention include those of metals in the di- or trivalent stage such as the chlorides of zinc, mercury, iron, copper, cadmium, bismuth, nickel, manganese and calcium, although other chlorides e.g. the chlorides of platinum, may also be used. Ferric chloride and zinc chloride are the preferred catalysts with zinc chloride being most preferred. The amount of metal chloride is suitably from 1 to 50%w, preferably from 15 to 35%w, based on weight of carrier.

Particularly suitable carriers for the catalysts of the invention are silica and alumina with silicas being preferred since they are more stable under the reaction conditions. The catalyst carriers for the process of the invention may be suitably obtained from commercial sources since there are commercially available aluminas and silicas having pore diameters of at least 30 m$\mu$. Other convention carriers having pore diameters of below 30 m$\mu$ may be treated by known techniques to increase the pore diameters thereof. Such treatments include steam and hydrothermal treatments. For example, hydrothermally treated silicas are usually prepared by immersing silica in water which is then heated in an autoclave at elevated temperatures e.g. at above 100° C. Steam treated silicas are usually prepared by heating silica in steam for from 2 to 24 hours at temperatures of from 600° to 1100° C.

Preferred silica carriers are those having average pore diameters of from 35 m$\mu$ to 1,000 m$\mu$ more preferably from 35 m$\mu$ to 500 m$\mu$. Suitable alumina carriers are those having average pore diameters of from 35 m$\mu$ to 10,000 m$\mu$. Such silica and alumina carriers generally have surface areas of from 1 to 150 m$^2$/g, preferably from 10 to 100 m$^2$/g, and pore volumes of from 0.4 to 1.5 ml/g.

The carrier may be calcined before and/or after being impregnated with the metal chloride. Quite suitably, the impregnated carriers are calcined at 150° to 600° C for from 0.4 to 3.0 hours. Calcination in this temperature range has little effect on the pore diameter of the carrier.

The reaction between the alpha olefin or alpha olefin mixture and hydrogen chloride may be carried out batch-wise or continuously and preferably the olefins are in the liquid state. The reaction is preferably carried out at elevated pressure e.g., from 2 to 30 atm, and at temperatures in the range of from 0° to 150° C. Suitable reaction times are from 0.4 to 6 hours. Typically, the hydrogen chloride will be employed in at least a stoichiometric amount with quantities in excess of stoichiometric e.g. 1.1 mole ratio of HCl/olefin or greater, being preferred.

EXAMPLES 1 to 7.

The catalysts used in these examples were prepared by impregnating the carriers described below with 25%w or 20%w of $ZnCl_2$, based on weight of carrier, followed by calcination for from 1 to 3 hours at 250 to 500° C. The carriers of catalysts (a) to (c) and (e) are prepared by a hydrothermal treatment of the silica carrier used for catalyst (f) whereas the carrier of catalyst (d) is prepared by a steam-treatment of the silica carrier used for catalyst (f). The carrier properties for catalysts (a) to (f) are given in Table I. For comparative purposes a further catalyst (g) comprising unsupported $ZnCl_2$ was also used.

Table I

| Catalyst | %w $ZnCl_2$ | Average Pore Diameter[1] mμ | Surface Area[2] M²/g | Pore Volume[3] ml/g |
|---|---|---|---|---|
| (a) | 25 | 250 | 28 | 1.0 |
| (b) | 20 | 260 | 27 | 1.0 |
| (c) | 20 | 46 | 94 | 1.0 |
| (d) | 20 | 150 | 17 | 0.65 |
| (e) | 20 | 300 | 10 | 1.2 |
| (f) | 20 | 14 | 282 | 1.0 |

[1] determined by mercury porosimetry (Carlo Erba; model 70)
[2] determined by BET method
[3] determined by water impregnation The above catalysts were used to prepare secondary alkyl chlorides from 1-tetradecene in the following manner.

The catalyst and olefin (about 150 g) were charged to a water-cooled autoclave. Hydrogen chloride was introduced until the required pressure was reached. After the end of the reaction the excess hydrogen chloride was stripped off and the reaction product washed several times with water and dilute sodium hydroxide. The products were analyzed by Gas Liquid Chromatography.

The reaction conditions and results are given in table II.

Table II

| Example | 1 | | 2 | | 3 | | 4 | 5 | 6 | 7 | |
|---|---|---|---|---|---|---|---|---|---|---|---|
| Catlyst | (a) | (f) | (a) | (f) | (a) | (f) | (b) | (c) | (e) | (d) | (g) |
| $ZnCl_2$/olefin molar ratio | 0.25 | 0.25 | 0.1 | 0.1 | 0.025 | 0.025 | 0.25 | 0.25 | 0.1 | 0.25 | 0.25 |
| Pressure (atm) | 5 | 5 | 10 | 10 | 20 | 20 | 5 | 5 | 10 | 5 | 5 |
| Temp.(° C) | 21–61 | 23–72 | 20–43 | 20–57 | 23–39 | 21–50 | 23–54 | 23–58 | 22–34 | 24–48 | 20–32 |
| Time (h) | 2 | 2 | 1.5 | 3 | 3 | 2.5 | 2.25 | 2.5 | 2.5 | 6.25 | |
| Olefin conversion (mol.%) | 100 | 100 | 100 | 100 | 100 | 100 | 99.6 | 99.6 | 95.8 | 99.3 | 96.4 |
| Isomer distribution % | | | | | | | | | | | |
| Internal | 0.6 | 4.0 | 1.2 | 3.0 | 0.6 | 2.8 | 1.7 | 2.1 | 2.0 | 1.6 | 3.7 |
| 3— | 10.3 | 16.8 | 10.6 | 14.1 | 12.9 | 15.8 | 8.0 | 11.2 | 4.8 | 8.7 | 17.0 |
| 2— | 89.1 | 79.2 | 88.2 | 82.9 | 86.5 | 81.4 | 90.3 | 86.7 | 93.2 | 89.7 | 79.3 |
| Isomer ratio | | | | | | | | | | | |
| 2/3 | 8.65 | 4.71 | 8.32 | 5.88 | 6.71 | 5.15 | 11.29 | 7.74 | 25.35 | 10.31 | 4.66 |
| 2/3 + internal | 8.17 | 3.81 | 7.47 | 4.85 | 6.41 | 4.32 | 9.31 | 6.52 | 15.13 | 8.71 | 3.83 |

EXAMPLE 8

1-Tetradecene was hydrochlorinated in a continuous manner by trickling olefin (LHSV of 8.2 ml/ml cat.h) in admixture with HCl, over 50 ml of catalyst (a) for 10 hours at a pressure of 20 atm and a temperature of 20° to 90° C. The results obtained were:

| Conversion | | 99.9 | % |
|---|---|---|---|
| Isomer distribution: | internal | 1.5 | % |
| | 3— | 10.5 | % |
| | 2— | 88 | % |
| Isomer ratio: | 2/3 | 8.41 | % |
| | 2/3 + internal | 7.33 | % |

EXAMPLE 9

The procedure of Examples 1 to 7 was repeated using catalysts (h) and (i) prepared by impregnating the silica carriers described below with 29.8%w of ferric chloride, based on weight of carriers, followed by calcination for 2 hours at 300° to 500° C. The carrier of catalyst (h) was hydrothermally treated silica having an average pore diameter of 114 mμ, a surface area of 35 m²/g and a pore volume of 1.0 ml/g (values determined by methods indicated in Table I). The carrier of catalyst (i) was the same as used for catalyst (f) of Examples 1 to 7.

The 1-tetradecene and HCl were reacted for 2 hours at 20 to 62° C and 10 atm. The molar ratio of $ZnCl_2$ olefin was 0.25. In both experiments the olefin conversion was 100%. The isomer distribution are ratios are given in Table III.

Table III

| Catalyst | (h) | (i) |
|---|---|---|
| Isomer distribution (%) | | |
| Internal | 4.3 | 6.6 |
| 3— | 20.5 | 22.3 |
| 2— | 75.2 | 71.1 |
| Isomer ratio | | |
| 2/3 | 3.67 | 3.19 |
| 2/3 + internal | 3.03 | 2.46 |

EXAMPLE 10

The procedure of Examples 1 to 7 was repeated using catalysts (j) and (k) prepared by impregnating the alumina carriers described below with 20%w of $ZnCl_2$, based on weight of carrier, followed by calcination for 1 hour at 500° C.

The alumina carrier of catalyst (j) was bimodal (two distinct groups of pores) having average pore diameters of 150 mμ (2/3 of total pore volume) and 4,200 mμ (1/3 of total pore volume), a surface area of 65 m²/g and a pore volume of 0.6 ml/g and the carrier of catalyst (k) had an average pore diameter of 11 mμ, a surface area of 200 m²/g and a pore volume of 0.6 ml/g (values determined by methods indicated in Table I).

The 1-tetradecene and HCl were reacted for 8 hours at 23° to 27° C over catalyst (j) and 4 hours at 23°–47° C over catalyst (k). The pressure was 5 atm and the $ZnCl_2$/olefin molar ratio was 0.24 in both cases. The conversions were 99.3 and 99.8 respectively. The isomer distribution and ratios are given in Table IV.

Table IV

| Catalyst | (j) | (k) |
|---|---|---|
| Isomer Distribution (%) | | |
| Internal | 1.1 | 2.7 |
| 3— | 5 | 11.7 |
| 2— | 93.9 | 85.6 |
| Isomer ratio | | |
| 2/3 | 18.8 | 7.32 |
| 2/3 + internal | 15.4 | 5.94 |

What is claimed is:

1. A process for the preparation of 2-chloroalkanes which comprises reacting a $C_7$ to $C_{30}$ alpha olefin or mixture of such olefins with hydrogen chloride in the presence of a metal chloride supported on a carrier having an average pore diameter of at least 30 m$\mu$.

2. The process according to claim 1, wherein the carrier is silica or alumina.

3. The process according to claim 2, wherein the carrier is a silica having a pore diameter of from 35 to 500 m$\mu$.

4. The process according to claim 3, wherein the carrier has a surface area of from 1 to 150 m$^2$/g.

5. The process according to claim 2, wherein the amount of metal chloride is from 1 to 50%w, based on weight of carrier.

6. The process according to claim 5, wherein the metal chloride is zinc chloride or ferric chloride.

7. The process according to claim 2, wherein the reaction pressure is from 2 to 30 atm.

8. The process according to claim 7, wherein the reaction temperature is from 0° to 150° C.

9. The process according to claim 2, wherein the alpha olefins are linear alpha-olefins.

* * * * *